United States Patent [19]

Altman

[11] Patent Number: 6,159,986
[45] Date of Patent: Dec. 12, 2000

[54] COMPOUNDS AND THERAPY FOR RESISTING MEMORY LOSS IN HUMANS

[76] Inventor: David A. Altman, 1165 Suffield, Birmingham, Mich. 48009

[21] Appl. No.: 09/431,868

[22] Filed: Nov. 2, 1999

[51] Int. Cl.[7] .......................... A01N 43/42; A01N 65/00; C07D 221/06
[52] U.S. Cl. ...................... 514/295; 424/195.1; 514/249; 514/261; 514/732; 514/738; 546/93; 546/97
[58] Field of Search .................... 424/195.1; 514/295, 514/732, 738, 249, 261; 546/93, 97

[56] References Cited

U.S. PATENT DOCUMENTS

| | | | |
|---|---|---|---|
| 4,898,891 | 2/1990 | Lavie et al. .................... | 514/732 |
| 5,049,589 | 9/1991 | Lavie et al. .................... | 514/732 |
| 5,106,979 | 4/1992 | Kozikowski et al. .......... | 546/93 |
| 5,506,271 | 4/1996 | Meruelo et al. ................ | 514/732 |
| 5,514,714 | 5/1996 | Meruelo et al. ................ | 514/561 |
| 5,820,867 | 10/1998 | Bewicke ......................... | 424/195.1 |
| 5,877,173 | 3/1999 | Olney et al. .................... | 514/217 |
| 5,889,033 | 3/1999 | Kaminski ........................ | 514/261 |
| 5,929,084 | 7/1999 | Zhu et al. ........................ | 514/295 |
| 5,985,282 | 11/1999 | Haveson ......................... | 424/195.1 |
| 5,989,919 | 3/1999 | Olney et al. .................... | 514/217 |
| 6,037,327 | 3/2000 | Castillo et al. ................. | 514/23 |

OTHER PUBLICATIONS

Computer Abstract EPAB Roumeliotis DE3935772 "PRPN of St Jhohn's Wort Extract Enriched With Hypericin . . .", Apr. 1991.

*Primary Examiner*—Herbert J. Lilling
*Attorney, Agent, or Firm*—Dobrusin Darden Thennisch & Loren PLLC

[57] ABSTRACT

Therapies and compounds for the inhibition of memory loss. In one embodiment, a combination of Huperzine A and hypericin is employed.

19 Claims, No Drawings

COMPOUNDS AND THERAPY FOR RESISTING MEMORY LOSS IN HUMANS

TECHNICAL FIELD

The present invention relates generally to the inhibition of memory impairment, and more particularly to compounds and therapies for the treatment of persons with Alzheimer's disease or other diseases affecting memory to help minimize the effects of memory impairment.

BACKGROUND ART

In recent years there has been a growing interest in the use of over the so counter supplements to help improve physical health and emotional well-being. Though not intended to diagnose, treat, cure or prevent any disease, so-called "home" or "natural" remedies have become popular substitutes for prescription drugs and other regulated substances.

By way of illustration, symptoms of depression and other cognitive functions are believed to be alleviated by the administration of St. John's Wort. Mental alertness and improved memory is believed to be improved through such supplements as Huperzine A (which has been noted in the art as an inhibitor of acetylcholinesterase).

Heretofore, the use of a combination therapy of available home remedy supplements for inhibiting the impairment of memory (e.g., rate of memory loss, memory content retention levels, etc.), from such diseases as Alzheimer's disease has not been explored.

SUMMARY OF THE INVENTION

The present invention overcomes the shortcomings of the prior art by providing compounds and therapies that help inhibit the impairment of memory. In a preferred embodiment of the present invention, an effective amount of a home remedy compound including a booster of the enzyme acetylcholine (e.g., without limitation, Huperzine A) is administered to a human being for improving memory. In a particularly preferred embodiment the acetylcholine-booster is compounded with a second component extracted from a suitable plant, such as an extract of hypericum perforatum, e.g., without limitation, hypericin.

The present compounds and therapies offer an attractive and low cost approach to the treatment of the deleterious effects of memory loss in mammals, and particularly human beings In one aspect, the starting materials are naturally-occurring and commercially available as over the counter supplements, thus making treatment in accordance with the present invention an attractive low cost alternative to many prescription remedies.

DETAILED DESCRIPTION OF PREFERRED EMBODIMENT

Unless otherwise specified, percentages are specified in weight. In a preferred embodiment of the present invention a compound including an effective amount of acetylcholine-booster (e.g., acetylcholinesterase-blocker) is adhered to a subject for inhibiting memory impairment (e.g., long or short term memory loss) of the subject. In a more preferred embodiment, the compound further includes, in combination with the acetylcholine booster, an extract from a plant hypeticum perforatum.

The preferred acetylcholiesterase-booster of the present invention preferably is a substantially purified compound derived from an herb. More specifically, it is the component known widely in the art as Huperzine A. As the skilled artisan will recognize, Huperzine A is but one of many recognized acetylcholine boosters. Others could work with similar efficacy (e.g., without limitation, Aricept). Thus, the present invention is not limited to the use only of Huperzine A.

In a preferred embodiment of the present invention, the acetylcholine booster is present in an amount sufficient to yield reproducible acetylcholine booster in the nervous system of a mammal. To illustrate, when the acetylcholine booster is Huperzine A, the amount of Huperzine A that is administered to a subject, in a typical dose, preferably ranges from about 0.01 to about 2 parts by weight, and more preferably up to about 0.2 and still more preferably to about 0.05 parts by weight of the overall compound.

It is believed that the efficacy of the acetylcholine-booster is substantially improved when it is administered in combination with a suitable amount of a plant extract from the plant of hypericum perforatum. A species of such extract is known in the art as St. John's Wort, a flowering plant, which can be grown under controlled conditions or harvested from the wild. In a particularly preferred embodiment, the specific extract hypericin is employed in the compounds and therapies of the present invention. When employed, the hypericum perforatum extract is employed in an amount up to about 6 parts, more preferably about 1.5 to about 4 parts by weight and still more preferably about 2.7 parts by weight of the overall compound.

As the skilled artisan will appreciate, concentrated or diluted forms of the present compounds may also be administered.

In a particularly preferred embodiment of the present invention, Huperzine A is used in combination with hypericin, e.g., administered separately or as a single compound. When employed in combination, about 1.5 parts to about 6 parts hypericin is used in combination with about 0.01 parts to about 2 parts Huperzine A. In another embodiment, the hypericin is used in about a 1:1 ratio with Huperzine A.

It is also contemplated that Huperzine is used in combination with St. John's Wort, which includes several forms of hypericin, flavenoids, and procyanidins. Thus, to illustrate, for a St. John's Wort supplement having about 0.3% hypericin, the combination of about 0.7 to about 2.8 parts St. John's Wort to about 0.01 to about 2 parts Huperzine A is employed, and more preferably about 1.4 parts by weight St. John's Wort to about 0.05 parts by weight Huperzine A.

It is further contemplated that an admixture of the acetylcholine-booster and extract from the plant of hypericum perforatum (which may be obtained from known solvent-based or solvent-free extraction processes) is compounded (e.g., using conventional techniques and using any suitable base, carriers or delivery agents) to form a single supplement to be ingested by a subject. For instance, it may be prepared in combination for ingestion or administration in a capsule, tablet, liquid or the lie. The supplement is packaged in any suitable manner, e.g. by placing in a suitably sealed container or in multiple containers of the respective ingredients, as part of a kit.

The therapies of the present invention can be administered in any suitable manner, including but not limited to orally, intravenously, intramuscularly, transdermally, inhalation, or the like.

In one combination therapy, the preferred dosage amount is about 0.1 milligrams to about 2 milligrams Huperzine A and about 0.7 to about 2.8 milligrams hypericin, and more preferably about 0.05 milligrams Huperzine A and about 1.4 milligrams hypericin per day for a person weighing about 70 kg (dosage amounts being adjustable upward and downward according to subject's weight, in a generally direct linear fashion (e.g., double the dose for double the weight). The therapy is continued for at least 3 days, more preferably at least 7 days, still more preferably at least about 10 day, and still more preferably greater than one month.

The skilled artisan will appreciate that other ingredients may be added to the combination of the present invention to tune the performance of the therapy. Without limitation, for instance, it is contemplated that antioxidants (e.g., Vitamins A,C, E, and beta carotene) may be employed to help the effects of aging. Examples of other ingredients include, for instance, ginkgo, ginseng, Echinacea, amino acids, folic acid, vitamins D, K and B group, creatine, fiber supplement, other over the counter supplements or mixtures thereof. Moreover, delivery enhancers may be employed to help improve absorption.

In a very specific illustrative example, twice a day, a human being weighing about 70 kg is administered orally a compounded tablet having as active ingredients about 1.4 mg of St. John's Wort and about 0.05 mg Huperzine A. After one month, the rate of memory impairment is shown to be inhibited as compared with subjects administered a placebo and those administered a like amount of Huperzine A or St. John's Wort individually. Like results are obtained for a similar composition, except containing about 0.5 mg.

What is claimed is:

1. A process for the inhibition of memory impairment in a mammal, comprising the steps of administering to a mammal an effective amount of about 0.1 to about 2 parts by weight of a total dose of Huperzine A and about 1.5 to about 6 parts by weight of a total dose of hypericin.

2. A process according to claim 1 wherein said Huperzine A is present in an amount up to about 0.2 parts by weight and said hypericin is present in an amount of about 2.7 parts by weight.

3. A process according to claim 1 further comprising compounding said combination into a single admixture prior to said administering step.

4. A compound for inhibiting memory loss, comprising an effective amount of a combination of about 0.1 to about 2 parts by weight of the compound of hypericin A and about 1.5 to about 6 parts by weight of the compound of hypericin.

5. A compound according to claim 4 wherein said Huperzine A is present in an amount of about 0.2 parts by weight of the compound and said hypericin is present in an amount of about 2.7 parts by weight of the compound.

6. A compound according to claim 4, wherein said compound is a solid.

7. A compound according to claim 4, wherein said compound is in a liquid.

8. A compound according to claim 4, further comprising an anti-oxidant.

9. A compound according to claim 4, further comprising Vitamin B.

10. A compound according to claim 4, further comprising Vitamin D.

11. A compound according to claim 4, further comprising Vitamin K.

12. A compound according to claim 4, further comprising gingko.

13. A compound according to claim 4, further comprising ginseng.

14. A compound according to claim 4, further comprising Echinacea.

15. A compound according to claim 4, further comprising amino acids.

16. A compound according to claim 4, further comprising folic acid.

17. A compound according to claim 4, further comprising creatine.

18. A compound according to claim 4, further comprising fiber supplement.

19. A process according to claim 1, wherein about 0.1 milligrams to about 2 milligrams Huperzine A and about 0.7 to about 2.8 milligrams hypericin are administered to a mammal per day per 70 kilograms of body weight of said mammal.

* * * * *

UNITED STATES PATENT AND TRADEMARK OFFICE
CERTIFICATE OF CORRECTION

PATENT NO.   : 6,159,986
DATED        : December 12, 2000
INVENTOR(S)  : David A. Altman It is certified that error appears in the above-identified patent and that said Letters Patent is hereby corrected as shown below:

Title page, item [56],
Attorney, Agent, or Firm replace "Dobrusin Darden Thennisch & Loren PLLC" with -- Dobrusin Darden Thennisch & Lorenz PLLC --.

Column 4,
Line 3, replace "hypericin" with -- Huperzine --.

Signed and Sealed this

Second Day of October, 2001

*Attest:*

*Attesting Officer*

NICHOLAS P. GODICI
*Acting Director of the United States Patent and Trademark Office*